(12) United States Patent
Cheng et al.

(10) Patent No.: US 8,538,733 B2
(45) Date of Patent: Sep. 17, 2013

(54) METHODS FOR THE ANALYSIS OF DISSOCIATION MELT CURVE DATA

(75) Inventors: Francis T. Cheng, Palo Alto, CA (US); Casey R. McFarland, San Francisco, CA (US)

(73) Assignee: Life Technologies Corporation, Carlsbad, CA (US)

( * ) Notice: Subject to any disclaimer, the term of this patent is extended or adjusted under 35 U.S.C. 154(b) by 464 days.

(21) Appl. No.: 12/359,241

(22) Filed: Jan. 23, 2009

(65) Prior Publication Data

US 2009/0204353 A1    Aug. 13, 2009

Related U.S. Application Data

(60) Provisional application No. 61/023,674, filed on Jan. 25, 2008.

(51) Int. Cl.
*H04B 15/00*    (2006.01)

(52) U.S. Cl.
USPC .............. 702/195; 374/1; 374/43; 374/137; 436/147; 702/19; 702/85; 702/130

(58) Field of Classification Search
USPC ............ 702/85, 19, 28, 49, 86, 99, 130, 195; 374/1, 43, 137; 436/147
See application file for complete search history.

(56) References Cited

U.S. PATENT DOCUMENTS

| 2004/0110219 A1* | 6/2004 | Buchholz et al. ................ 435/6 |
| 2006/0094108 A1* | 5/2006 | Yoder et al. ................ 435/287.2 |
| 2007/0026421 A1* | 2/2007 | Sundberg et al. ................ 435/6 |
| 2007/0154980 A1* | 7/2007 | Gasper et al. ................ 435/40.5 |
| 2008/0003649 A1* | 1/2008 | Maltezos et al. ............. 435/91.2 |
| 2009/0222503 A1* | 9/2009 | Palais et al. .................... 708/277 |

FOREIGN PATENT DOCUMENTS

| WO | WO-01/53822 | 7/2001 |
| WO | WO-2005/064012 | 7/2005 |
| WO | WO-2007/035806 | 3/2007 |

OTHER PUBLICATIONS

Al-Robaiy, S. et al., "Rapid Competitive PCR using Melting Curve Analysis for DNA Quantification", *Biotechniques*, Informa Life Sciences Publishing vol. 31, No. 6, Dec. 1, 2001, 1382-1387 pgs.
Sanchez, J. Aquiles et al., "Linear After the Exponential (Late)—PCR: An advanced method of asymmetric PCR and its uses in quantitative real time analysis", *Proceedings of the National Academy of Sciences*, National Academy of Science, Washington DC, vol. 101, No. 7, Feb. 17, 2004, 1933-1938 pgs.

(Continued)

*Primary Examiner* — Alexander H Taningco
*Assistant Examiner* — Paul D Lee

(57) ABSTRACT

Methods are provided that operate on raw dissociation data and dissociation curves to generate calibrations of the detected data and to further improve analysis of the data. The data can be taken from each support region of a multi-region platform, for example, from each well of a multi-well plate. Each support region can be loaded with portions of the same sample. In some embodiments, a dissociation curve correction can be calibrated for the sample, prior to a run of an experiment using such sample. In some embodiments, a method is provided for generating a melting transition region of dissociation curves that show the melting characteristics of the sample. In some embodiments, dye temperature dependence correction can be performed on the dissociation curve data to further improve analysis. In some embodiments, a feature vector can be derived from the melt data, and the feature vector can be used to further improve genotyping analysis of the dissociation curves.

22 Claims, 12 Drawing Sheets

(56) References Cited

OTHER PUBLICATIONS

Pals, G. et al., "A Rapid and Senstitive Approach to Mutation Detection Using Real-Time Polymerase Chain Reaction and Melting Curve Analyses, Using BRCA1 as an Example", *Molecular Diagnosis*, Naperville, IL, vol. 4, No. 3, Sep. 1, 1999, 241-246 pgs.
International Search Report for Int'l Application No. PCT/US09/032049, along with the PCT Written Opinion, mailed Jun. 3, 2009.
Wittwer, C. T. et al., "Continuous Fluorescence Monitoring of Rapid Cycle DNA Amplification", *Biotechniques*, Informa Life Sciences Publishing, Westborough, MA, vol. 22, No. 1, Jan. 1, 1997, 130/131, 134-138 pgs.
Chinese Search Report for application No. 200980110889.6 dated Dec. 5, 2012.

\* cited by examiner

| | Sample Genotype ID | Uncorrected MCD(40%) | Corrected MCD(90%) | | Sample Genotype ID | Uncorrected MCD(40%) | Corrected MCD(90%) | | Sample Genotype ID | Uncorrected MCD(40%) | Corrected MCD(90%) |
|---|---|---|---|---|---|---|---|---|---|---|---|
| 1 | NTC | variant | variant | 33 | hom | hom | Hom | 65 | hom | wt | hom |
| 2 | wt | wt | wt | 34 | wt | hom | wt | 66 | het | het | het |
| 3 | het | wt | het | 35 | het | het | het | 67 | het | wt | het |
| 4 | het | wt | het | 36 | unknown | wt | hom | 68 | het | wt | het |
| 5 | het | wt | het | 37 | wt | wt | wt | 69 | hom | wt | hom |
| 6 | wt | hom | wt | 38 | hom | wt | hom | 70 | hom | wt | hom |
| 7 | wt | hom | het | 39 | het | het | het | 71 | hom | wt | hom |
| 8 | wt | hom | wt | 40 | hom | wt | hom | 72 | hom | wt | hom |
| 9 | hom | hom | hom | 41 | het | het | het | 73 | hom | wt | hom |
| 10 | hom | wt | hom | 42 | hom | hom | hom | 74 | hom | wt | het |
| 11 | hom | wt | hom | 43 | het | het | het | 75 | het | wt | het |
| 12 | wt | wt | wt | 44 | het | het | het | 76 | het | het | het |
| 13 | het | wt | het | 45 | het | het | het | 77 | het | wt | het |
| 14 | het | wt | het | 46 | het | het | het | 78 | het | wt | variant |
| 15 | het | wt | het | 47 | het | het | het | 79 | wt | hom | wt |
| 16 | het | wt | het | 48 | ntc | variant | variant | 80 | het | wt | het |
| 17 | het | wt | variant | 49 | hom | wt | hom | 81 | het | het | het |
| 18 | hom | wt | hom | 50 | hom | wt | hom | 82 | hom | wt | het |
| 19 | hom | wt | hom | 51 | hom | hom | hom | 83 | het | wt | het |
| 20 | het | het | het | 52 | het | het | het | 84 | het | variant | variant |
| 21 | hom | hom | het | 53 | het | het | het | 85 | hom | wt | hom |
| 22 | het | het | het | 54 | hom | hom | hom | 86 | hom | wt | hom |
| 23 | het | wt | het | 55 | het | het | het | 87 | wt | wt | wt |
| 24 | het | wt | het | 56 | het | het | het | 88 | het | het | het |
| 25 | het | wt | het | 57 | het | het | het | 89 | hom | wt | hom |
| 26 | het | wt | het | 58 | het | het | het | 90 | hom | wt | hom |
| 27 | het | het | het | 59 | ntc | hom | variant | 91 | het | wt | het |
| 28 | het | het | het | 60 | hom | hom | hom | 92 | het | wt | het |
| 29 | het | het | het | 61 | hom | wt | hom | 93 | hom | wt | hom |
| 30 | wt | hom | wt | 62 | het | wt | het | 94 | hom | wt | hom |
| 31 | wt | hom | wt | 63 | hom | wt | hom | 95 | hom | wt | hom |
| 32 | het | het | het | 64 | het | het | het | 96 | ntc | variant | variant |

FIG. 10

| Sample ID | $T_m$ | Delta Max | $T_{DeltaMax}$ | Sum of Absolute Difference (SAD) |
|---|---|---|---|---|
| 1. Wild Type | 83.9 | 0.0 | N/A | 0.0 |
| 2. Het 5 | 84.1 | 18.5 | 82.1 | 555.8 |
| 3. Het 14 | 84.2 | 35.2 | 84.2 | 1113.4 |
| 4. Het 11 | 84.2 | 49.1 | 84.0 | 1524.4 |
| 5. Het 4 | 84.3 | 41.3 | 84.2 | 1119.9 |
| 6. Het 10 | 84.3 | 51.4 | 84.2 | 1482.7 |
| 7. Het 6 | 84.3 | 57.0 | 84.2 | 1686.2 |
| 8. Het 8 | 84.3 | 65.8 | 84.1 | 2294.5 |
| 9. Het 3 | 84.3 | 65.9 | 84.2 | 2045.6 |
| 10. Het 7 | 84.3 | 74.5 | 84.1 | 2444.2 |
| 11. Het 12 | 84.4 | 82.9 | 84.2 | 2537.8 |
| 12. Het 9 | 84.5 | 73.7 | 84.3 | 1782.6 |
| 13. Het 13 | 84.5 | 100.0 | 84.2 | 3260.9 |

FIG. 11

METHODS FOR THE ANALYSIS OF DISSOCIATION MELT CURVE DATA

FIELD

The field of disclosure of relates to methods for analyzing melt curve data, especially as the analysis relates to data for which the melting temperatures of the plurality of samples varies by only a fraction of a degree.

BACKGROUND

DNA amplification methods provide a powerful and widely used tool for genomic analysis. Polymerase chain reaction (PCR) methods, for example, permit quantitative analysis to determine DNA copy number, sample source quantitation, and transcription analysis of gene expression. Melting curve analysis is an important tool used to discriminate real amplification products from artifacts, for genotyping, and for mutation scanning. DNA analysis methods allow the detection of single base changes in specific regions of the genome, such as single nucleotide polymorphisms (SNPs). SNP analysis and other techniques facilitate the identification of mutations associated with specific diseases and conditions, such as various cancers, thalassemia, or others.

Statistical assay variations in melt curve data result from system noise in an analysis system, such as the thermal non-uniformity of a thermocycler block in a thermal cycler apparatus. For certain genotyping applications, the melting point shift between samples may be only fractions of a degree. In the case of SNP analysis, the SNP mutations may shift the melting point temperature by no more than 0.2° C.

Accordingly, there is a need in the art for methods of analyzing small differences in melting curves in the presence of the inherent noise of the analysis.

BRIEF DESCRIPTION OF THE DRAWINGS

FIG. 10 is a set of experimental data that has been analyzed according to various embodiments of methods for the analysis of dissociation melt curve data.

FIG. 11 is a set of experimental data that has been analyzed according to various embodiments of methods for the analysis of dissociation melt curve data.

DETAILED DESCRIPTION

Figure 1:
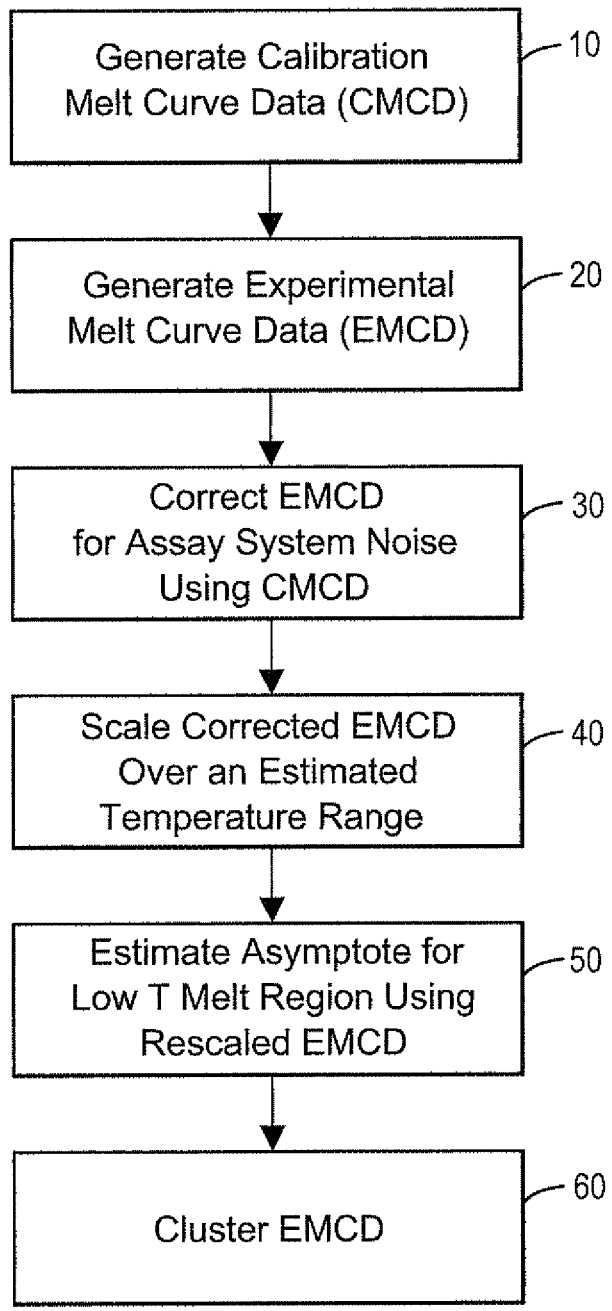
FIG. 1 is a flow chart that depicts various embodiments of methods for the analysis of dissociation melt curve data.

What is disclosed herein are various embodiments of methods for analyzing dissociation melt curve data, or as it is used throughout herein, melt curve data (MCD), where the differences in the melting points between various samples are small. For example, various embodiments of methods for analyzing dissociation melt curve data address samples sets where the differences in melting points may vary by only fractions of degrees. According to various embodiments of methods for the analysis of dissociation melt curve data, a calibration set of melt curve data may be used as a basis for correcting experimental sets of melt curve data, for example, with respect to assay system variance or noise. According to various embodiments, the melt curve data may be processed using curve-fitting techniques. In various embodiments of methods for analyzing dissociation melt curve data, different attributes of dissociation melt curve data, such those generated using a difference plot, may be used as the basis of cluster analysis of experimental melt curve data.

One known approach for DNA melting curve analysis utilizes fluorescence monitoring with intercalating double-strand-DNA specific dyes, such as for example, SYBR Green. The SYBR Green dye attaches to the DNA as double-stranded DNA amplification products are formed, and continues to bind to the DNA as long as the DNA remains double-stranded. When melting temperatures are reached, the denaturation or melting of the double-stranded DNA is indicated and can be observed by a significant reduction in fluorescence, as SYBR Green dissociates from the melted strand. The detected dye fluorescence intensity typically decreases about 1000-fold during the melting process. Plotting fluorescence as a function of temperature as the sample heats through the dissociation temperature produces a DNA melting curve. The shape and position of the DNA melting curve is a function of the DNA sequence, length, and GC/AT content.

Further, various approaches for validating the integrity of PCR reactions rely on melting curve analysis to discriminate artifact from real amplification product. Melting curve analysis can also be used to differentiate the various products of multiplexed DNA amplification, and to extend the dynamic range of quantitative PCR. DNA melting curve analysis is also used as a powerful tool for optimizing PCR thermal cycling conditions, because the point at which DNA fragments or other material melts and separate can be more accurately pinpointed.

In some embodiments, dissociation curve analysis methods calculate and display the first derivative of multi-component dye intensity data versus temperature, i.e., the differential melting curve. The melting temperature, $T_m$, at a peak of the differential melting curve can be used to characterize the product of a biochemical reaction. A sample with multiple amplification products will show multiple peaks in the differential melt curve. In some embodiments, melting curve detection involves very precise measurements of temperature and allows for the identification of a sample using the melting temperature, $T_m$. The determination of $T_m$ using various embodiments of methods for differential dissociation and melting curve detection is disclosed in related in U.S. patent application Ser. No. 12/020,369, which is incorporated herein by reference in its entirety.

Figure 3A:
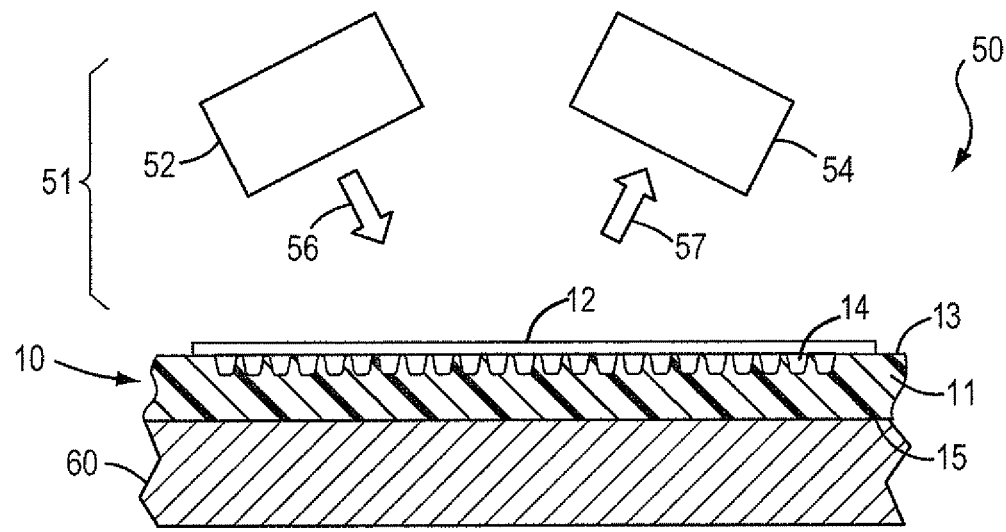
FIG. 3A and FIG. 3B depict a generalized schematic of a thermal cycler system.
Figure 3B:
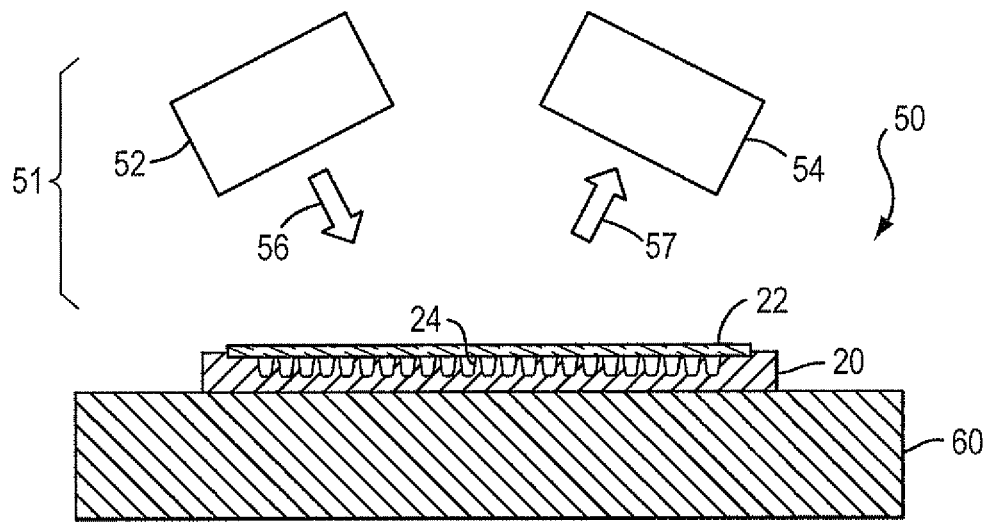

According to various embodiments as shown in FIG. 3A and FIG. 3B, a sample can be loaded into a sample support device. In various embodiments, as shown in FIG. 3A, a sample support device 10 comprises a substrate 11 having substantially planar upper and lower surfaces, 13, 15, respectively. Various embodiments of a sample support device may have a plurality of sample regions 14 on a surface 13. In various embodiments, the substrate 11 may be a glass or plastic slide with a plurality of sample regions 14, which may be isolated from the ambient by cover 12. Some examples of a sample support device may include, but are not limited by, a multi-well plate, such as a standard microtiter 96-well, a 384-well plate, or a microcard, as depicted in sample support device 20 of FIG. 3B, having a plurality of sample regions or wells 24, which may be isolated from ambient by cover 22. The sample regions in various embodiments of a sample support device may include depressions, indentations, ridges, and combinations thereof patterned in regular or irregular arrays on the surface of the substrate. In FIG. 3A and FIG. 3B, a sample support device is shown placed in a thermal cycler system. In various embodiments of a thermal cycler system, there may be a heat block, 60, and a detection system 51. The detection system 51 may have an illumination source 52 that emits electromagnetic energy 56, and a detector 54, for receiving electromagnetic energy 57 from samples in sample support devices 10 and 20 in FIG. 3A and FIG. 3B, respectively.

In various embodiments, replicate aliquots of a sample can be loaded into the plate to determine the melting temperature, Tm, of the each well. Ideally, these temperatures should be identical throughout the wells, given that the samples are replicates, In practice, variations in the analysis system, for example, non-uniformity of heating elements of the analysis system, create variations in the set of replicates. According to various embodiments of methods for the analysis of dissociation melt curve data, such melt curve data using replicates may be used as a calibration set of data. In FIG. 1, step 10, such a plurality of melting points comprises a plurality or set of calibration melt curve data (CMCD). Similarly, as indicated in step 20 of FIG. 1, in a separate sample plate, unknown samples of interest for analysis may be dispensed into a plurality of support regions of a sample support device to determine the melting temperature of the unknown samples. Such a plurality of melting points comprises a plurality or set of experimental melt curve data (EMCD).

According to various embodiments of methods for the analysis of dissociation melt curve data, as depicted in step 30 of FIG. 1, signal processing steps may be applied to the raw dissociation melt curve data in advance of subsequent steps, such scaling, curve fitting, and cluster analysis. Such signal processing steps may include the correction of the EMCD with respect to assay system variance or noise. Sources of assay systems noise may include, for example, but not limited by, thermal non-uniformity, excitation source non-uniformity, and detection source noise.

According to various embodiments as indicated in FIG. 1 step 40, melt curve data may be processed to remove information that is not relevant for defining true differences among dissociation melt curves having melting temperatures that are different by only fractions of a degree, by scaling the data over an estimated temperature range.

Figure 4:
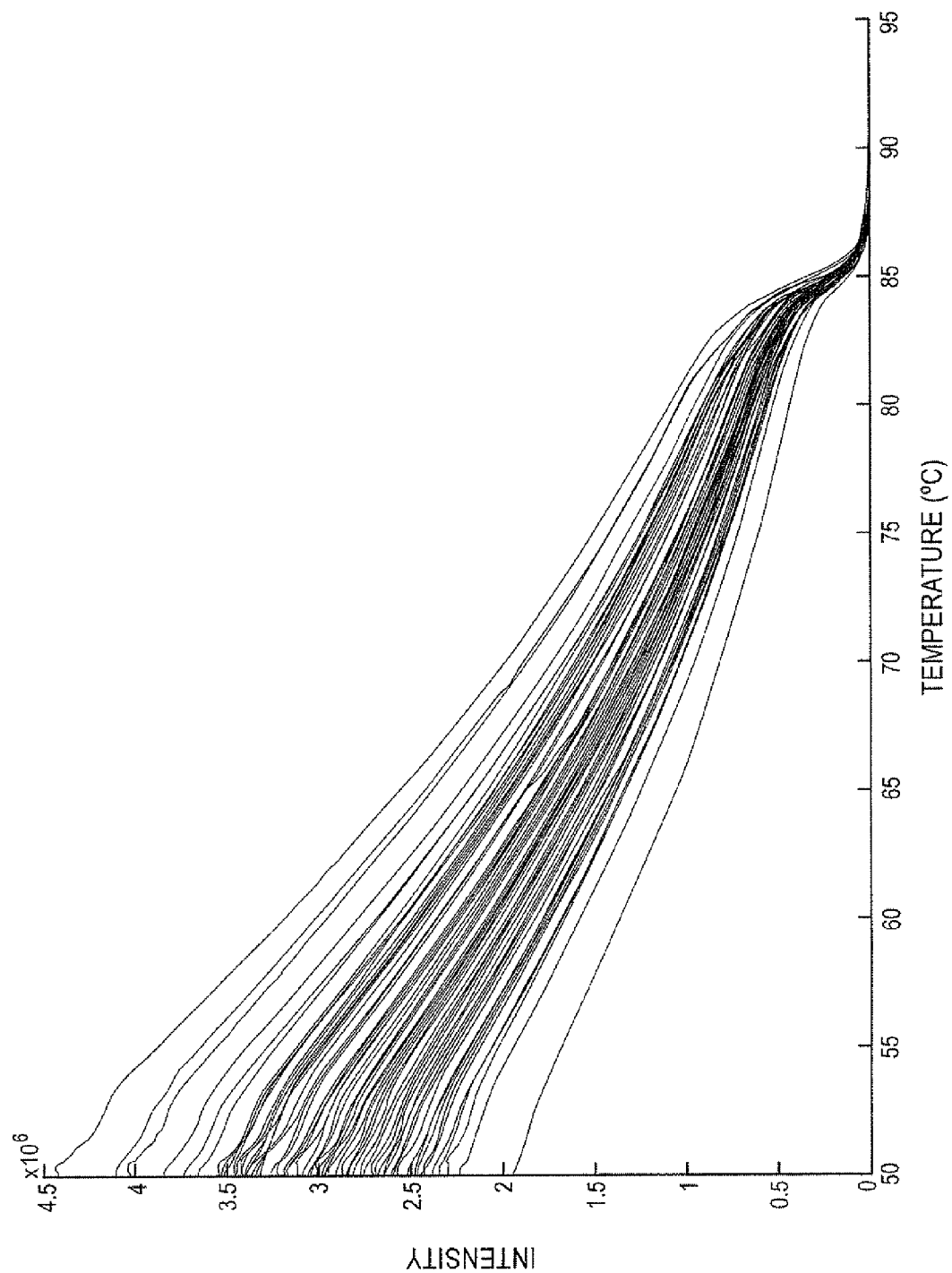
FIG. 4 depicts a series of dissociation melt curves for a set of calibration data.

For example, in FIG. 4, by using a set of CMCD, various embodiments of step 40 of FIG. 1 may be illustrated. The CMCD shown in FIG. 4 represents 96 replicates of a sample, where intensity of the signal is plotted as a function of temperature. Between 50° C. and 55° C., in the low temperature region of the curve, there are deviations from linearity that are artifacts, which are irrelevant to the melt curve data. Further, by inspecting FIG. 4, it is apparent that the melting occurs in a region of between about 70° C. to about 90° C. and that intensity approaches zero at temperatures above the melt. Additionally, the region from about 55° C. to about 80° C. a monotonic decrease in intensity is apparent. This is due to a decrease in the light emitted from the replicates as a result of the temperature dependence of dye emission, which is known to be an inverse relationship (i.e. dye emission decreases as temperature increases).

According to various embodiments of methods for the analysis of dissociation melt curve data as depicted in step 40 of FIG. 1, curve-fitting of the calibration data may be done based on the observations that the region between about 50° C. to about 55° C. contains artifacts, the region between 55° C. to about 80° C. should be linear, the melt occurs between about 70° C. to about 90° C., and the high temperature region above the melt approaches zero. In various embodiments, the curve-fitting of the calibration data may additionally use the information from a reference well in the calibration set. For example, a reference well may be selected as the initially brightest well in a calibration set before the melt curve analysis is run. A first derivative may be taken on the reference well melt curve data after the analysis is complete. The width of the first derivative peak of a reference well may be used in conjunction with the observation that the melting occurs in a region of between about 70° C. to about 90° C. to define the abscissa. Additionally, given that it is known that the region between 55° C. to about 80° C. should be linear, the ordinate may be scaled using a relative scale, wherein a maximum value of the ordinate scale is set by an intercept of the low temperature end of the melt curve data with the ordinate, and should approach zero at the high temperature range of the melt curve profile.

Figure 5:
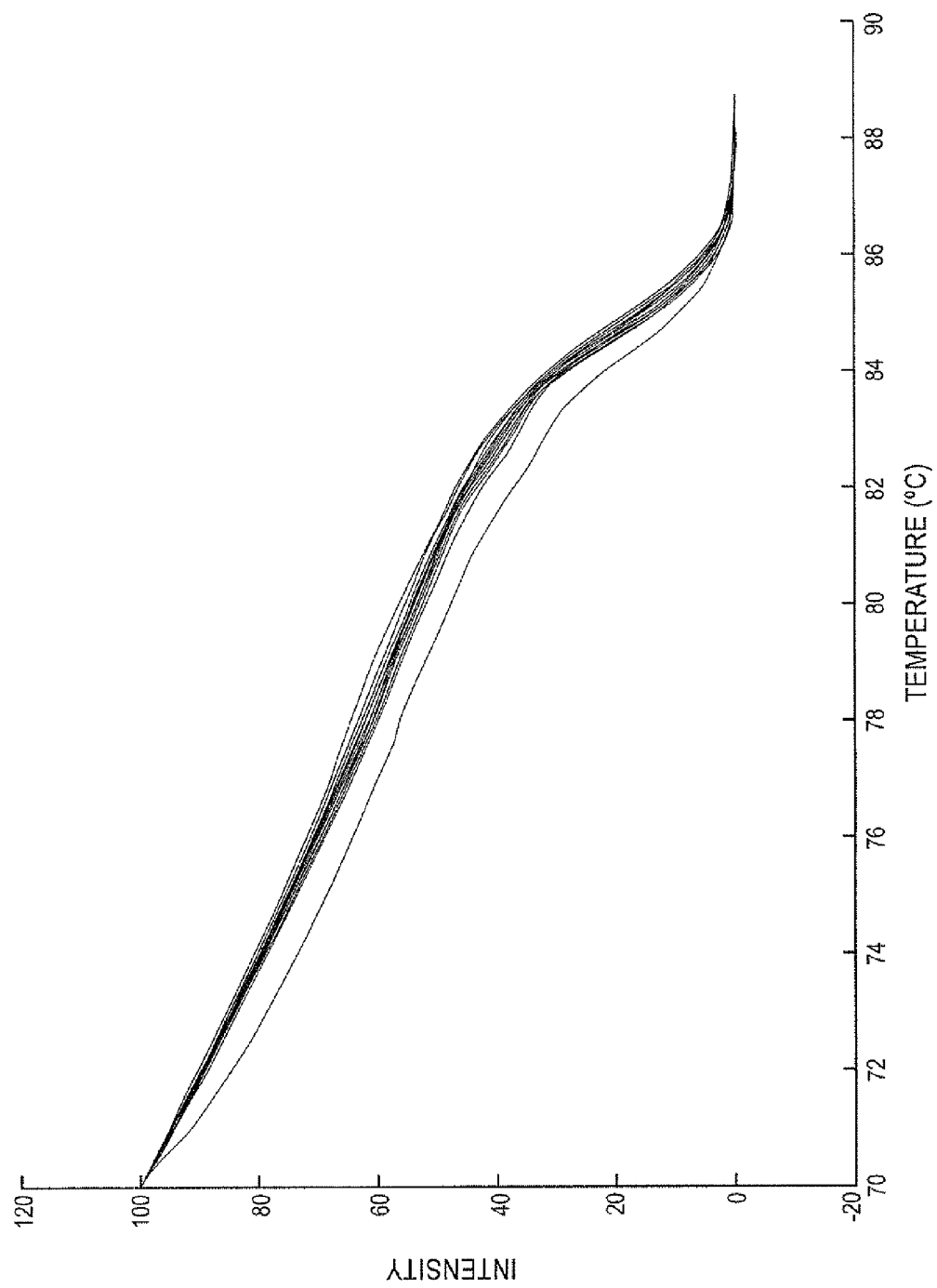
FIG. 5 depicts the series of graphs of FIG. 4 taken over an estimated temperature range according to various embodiments of methods for the analysis of dissociation melt curve data.

According to various embodiments of step 40 of FIG. 1, for the purpose of illustration, the CMCD of FIG. 4 has been scaled to produce the melt curve data shown in FIG. 5. For FIG. 5, the calibration data of FIG. 4 have been fit to an abscissa scaled to between about 70° C. to about 88° C. Additionally, the linear portion of the low melt end of the CMCD have been fit to 100 at intercept at the low temperature end of the scale, and approach zero at the high temperature range of the melt curve profile.

In various embodiments of methods for the analysis of dissociation melt curve data, in addition to the curve-fitting of step 40 of FIG. 1, additional curve-fitting steps may be applied to the calibration data. For example, as indicated in step 50 of FIG. 1, according to various embodiments, it may be desirable to estimate an asymptote at the low temperature end of the curve for the purpose of detecting differences in data sets of melt curve data that have melting temperatures that vary by only fractions of a degree. Various embodiments for estimating an asymptote for the low temperature end of the melt curve data are depicted in FIGS. 6A and 6B.

Figure 6A:
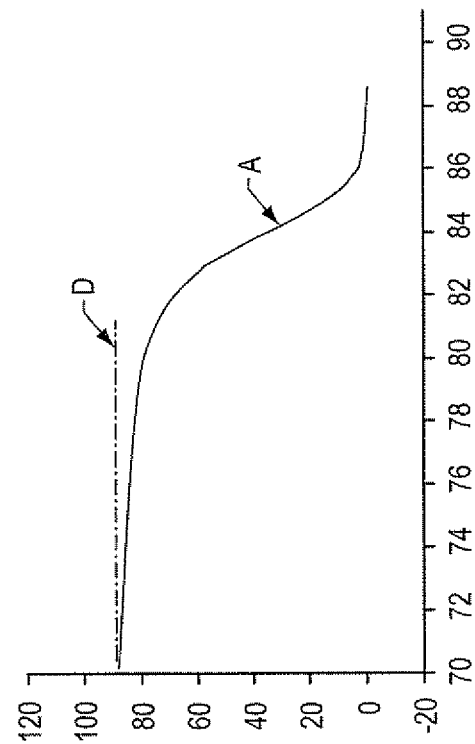
FIG. 6A and FIG. 6B illustrate estimating an asymptote according to various embodiments of methods for the analysis of dissociation melt curve data for the low temperature region of graphs, such as those shown in FIG. 5.
Figure 6B:
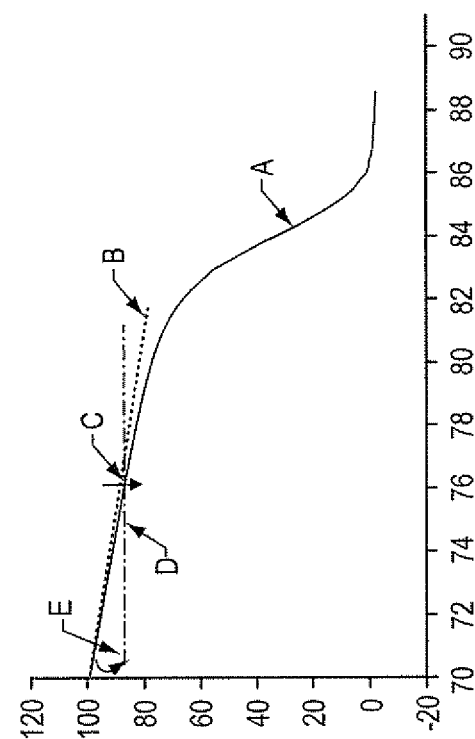

In FIG. 6A, line B may be extrapolated from a melt curve A by selecting a linear portion over a narrow region of the low temperature melt range. The linear portion may be selected, according to various embodiments, by an interval of a temperature change at a defined temperature point. According to various embodiments, the defined temperature point may be selected using the first derivative data, and defining a transition region, as for example, but not limited by, the full width at half the maximum of the first derivative peak. As one of ordinary skill in the art is apprised, such a transition region corresponds to an interval of two standard deviations about the midpoint of the first derivative curve. As such, other intervals about the curve may also be selected. In various embodiments, a temperature point may be selected at the low temperature end of the defined transition region, as the low temperature region is known to be linear. According to various embodiments, after a temperature point is selected, an interval from the point containing enough data points to extrapolate a line is selected. In that regard, the interval would correspond to at least two data points. According to various embodiments, the interval may be at least about 0.1° C. In various embodiments, the interval may be at least about 0.5° C. In still other embodiments, the interval may be at least about 1° C.

Figure 7:
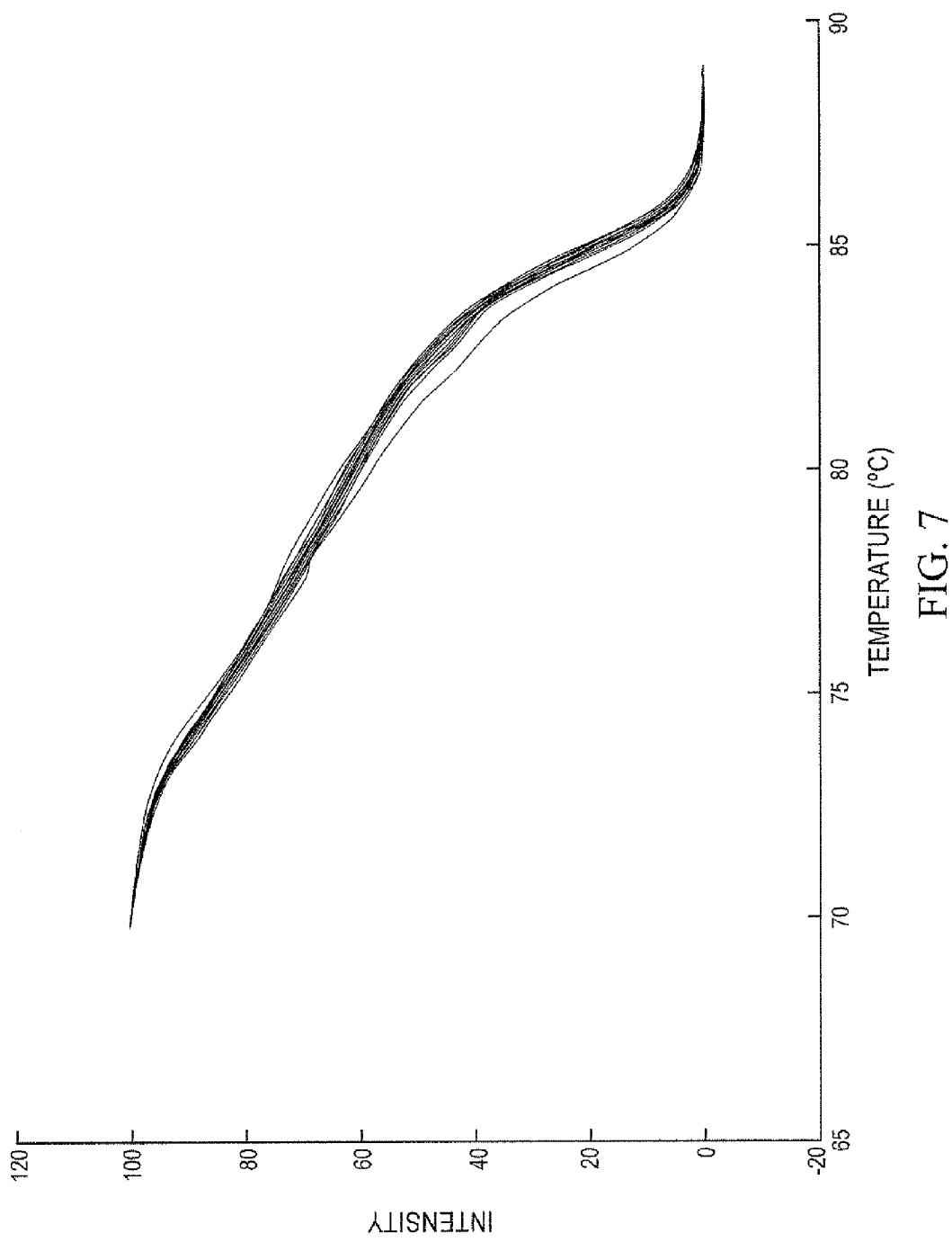
FIG. 7 depicts the series of graphs of FIG. 5 redrawn according to various embodiments of methods for the analysis of dissociation melt curve data shown in FIG. 6A and FIG. 6B.

For example a temperature point of about 70.0° C. may be selected, with an interval of plus or minus 0.5° C. around the temperature point. From this narrow linear region, a line, such as line B in FIG. 6A can be extrapolated. An algorithm, such as the subtraction of melt curve A and line B, can be used to evaluate a point where the two functions deviate by preset limit. For example, but not limited by, when the difference between the two curves is at least as great as, for example, twice the assay noise, then the calculated difference may indicate a significant difference. Alternatively, in various embodiments, other methods for determining a point where the two functions deviate by preset limit, such as the method for detecting nonlinearity in analog circuit analysis, may be used. Such a preset limit is designated as point C in FIG. 6A. Point C defines a point through which line D is drawn horizontally through the ordinate, thereby defining an estimated asymptote for the low temperature region. The calibration melt curve A is then fit accordingly to this asymptote, line D, as shown in FIG. 6B. In FIG. 7, the calibration data of FIG. 5 have been fit to an estimated low temperature asymptote.

Figure 8:
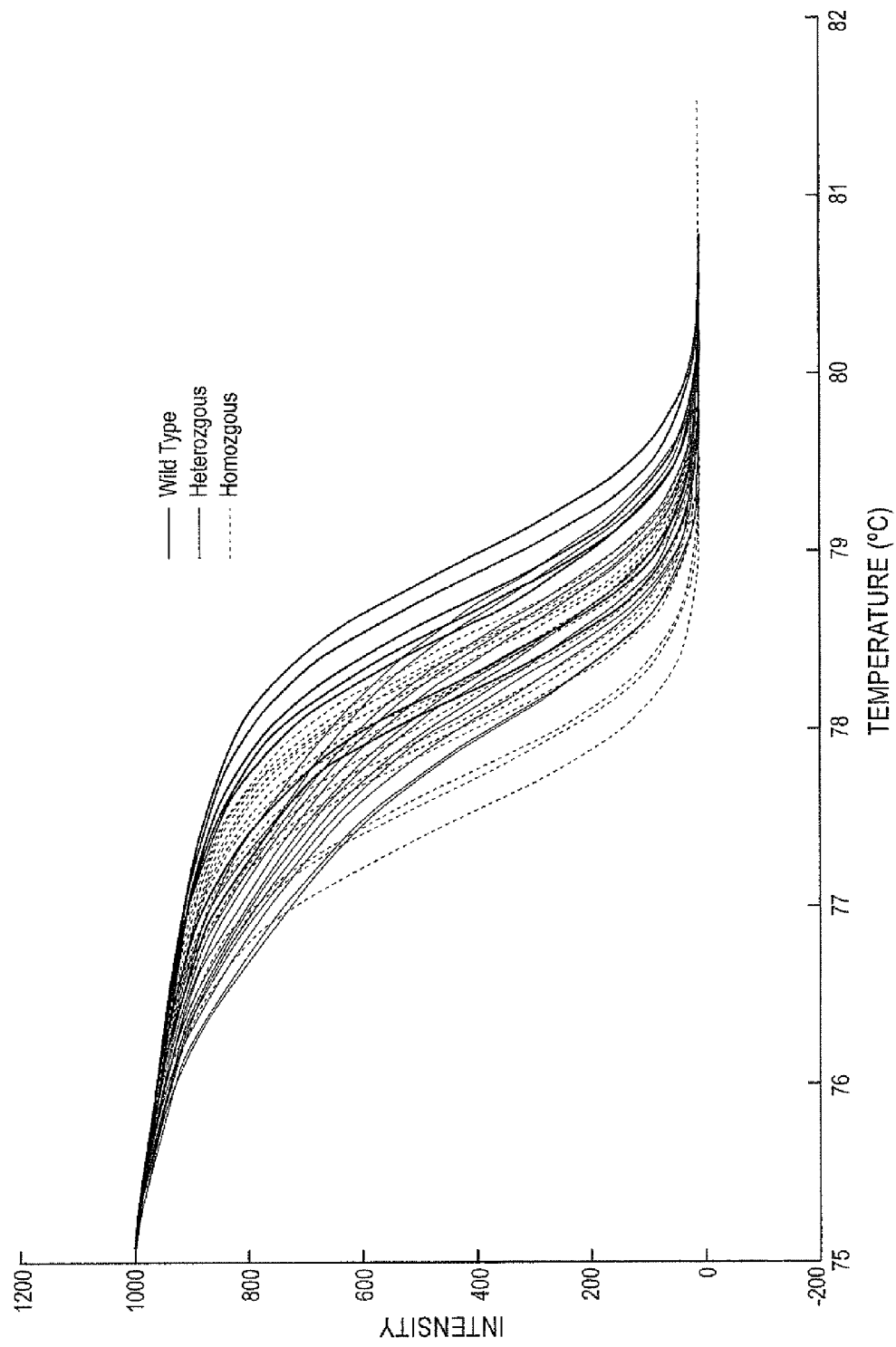
FIG. 8 depicts a series of dissociation melt curves for a set of experimental data according to various embodiments of methods for the analysis of dissociation melt curve data.

Step 40 and step 50 in FIG. 1 can be applied to a set of experimental data generated using test samples. The data presented in FIG. 8 represent a set of experimental data that have been fit according to various embodiments of methods described by step 40 and step 50 of FIG. 1. The EMCD in FIG. 8 have been clustered according genotype. In inspecting the EMCD of FIG. 8, there appears to be significant overlap of the melt curve data for the genotypes.

As previously mentioned, as depicted in step 30 of FIG. 1, according to various embodiments, signal processing steps may be applied to the raw dissociation melt curve data in advance of steps, such as steps 40 and 60 of FIG. 1. Such signal processing steps may include the correction of the EMCD with respect to assay system variance or noise, such as, but not limited by, assay system thermal non-uniformities inherent in thermal cycler systems.

As previously stated, the calibration melt curve data set is generated from replicates of the same sample dispensed in support regions of a sample support device, the variations in the calibration data are due to the inherent assay system noise. Accordingly, the information in the calibration melt curve data can be used to correct the experimental melt curve data for system noise. For example, a reference sample region in the EMCD may be selected. According to various embodiments, the frequency plot of the intensities of the sample regions, such as a well, in a sample support device may be determined, and a sample region within two standard deviations of the peak intensity of the EMCD may be selected as a reference sample region. In various embodiments, the reference sample region of the EMCD corresponding to the greatest intensity may be selected, however any sample region within two standard deviations would not be an outlier; i.e. either too dim or to bright, for the purpose of selecting a reference sample region, such as a well. According to various embodiments for correcting system noise as indicated in step 20 of FIG. 1, the corresponding sample region for the CMCD is then selected as a CMCD reference sample region, such as a well. In various embodiments, a difference from the CMDC reference sample region to any sample region on the sample support may be calculated for any point along the melt curve data, or any form of the melt curve data, such as, but not limited by, derivative data. This correction of the variation of the sample support regions over the sample support device due to assay system noise may then be applied to the EMCD. Other types of approaches may be used to determine a correction factor. For example, an average of the intensities of the CMCD may be taken over the entire CMCD sample set. For any specific sample region of the CMCD, a correction may be determined by subtracting the sample region intensity from the average. That correction may then be applied to the corresponding sample region of the EMCD.

Figure 9:
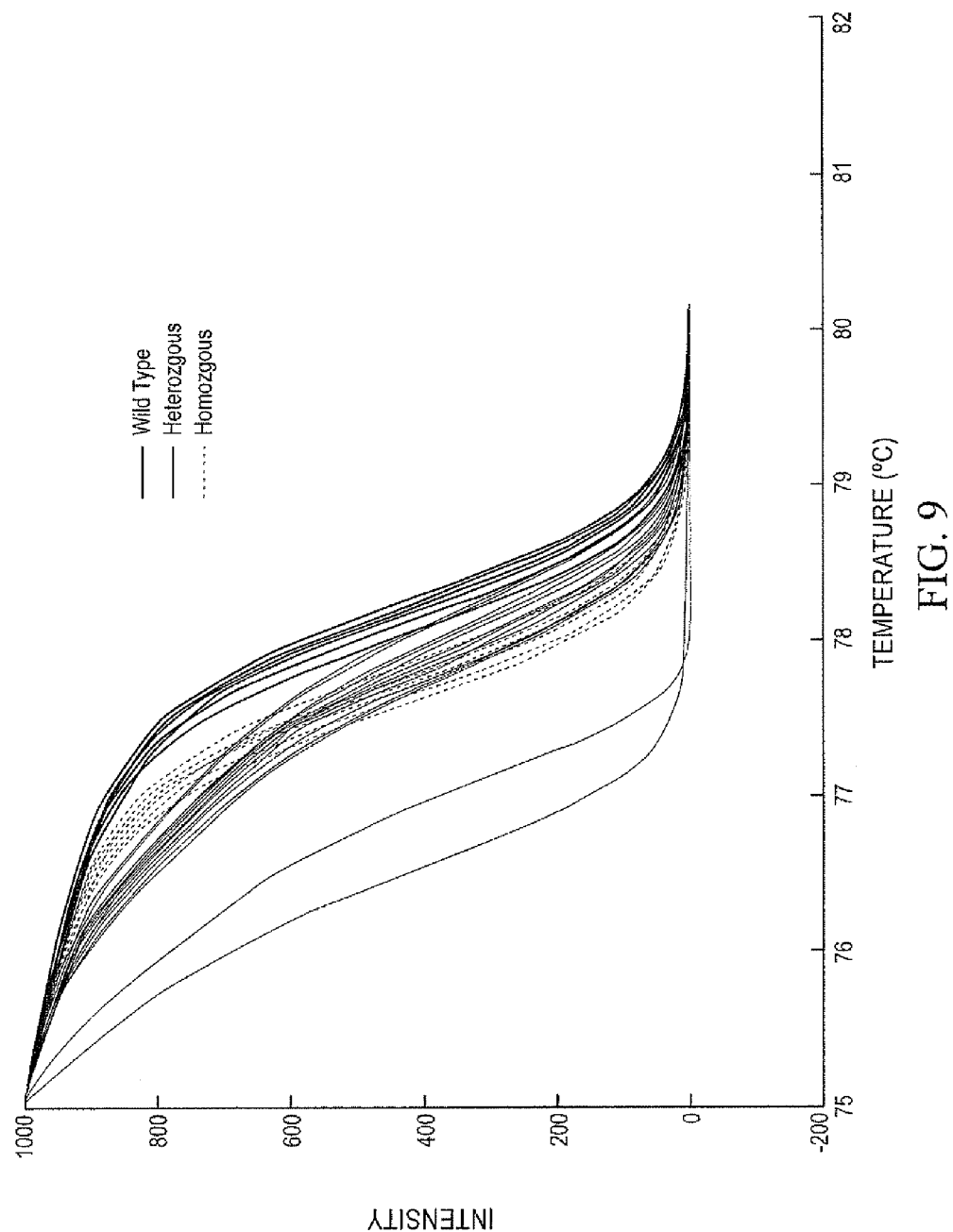
FIG. 9 depicts the series of graphs of FIG. 8 which have been corrected for assay system variance or noise according to various embodiments of methods for the analysis of dissociation melt curve data.

A correction as described above for step 20 of FIG. 1 was applied to FIG. 8, and the result is demonstrated in FIG. 9. It is apparent that the correction of the experimental data as displayed in FIG. 9 results in the ready clustering of the genotypes. A set of EMCD shown in tabular form is presented in FIG. 10. In FIG. 10, the first column displays the previously verified genotype of the samples. The second column represents the call made based on experimental data that was not corrected for assay system noise using calibration data. Finally, the third column represents the call made based on experimental data that was corrected for assay system noise using calibration data. As can be seen in the heading, the calls made using the uncorrected experimental data were correct 40% of the time, while the calls made using the corrected experimental data were correct 90% of the time. Moreover, the samples marked "ntc" are no-template controls, are negative controls for which no melt curve would be expected. The corrected MCD consistently assigns the negative controls correctly. Accordingly, various embodiments of methods for the analysis of dissociation melt curve data as depicted in FIG. 1 are effective in making determinations of genotyping, where the melting temperatures in an experimental set of data are different by only fractions of a degree.

Figure 12:
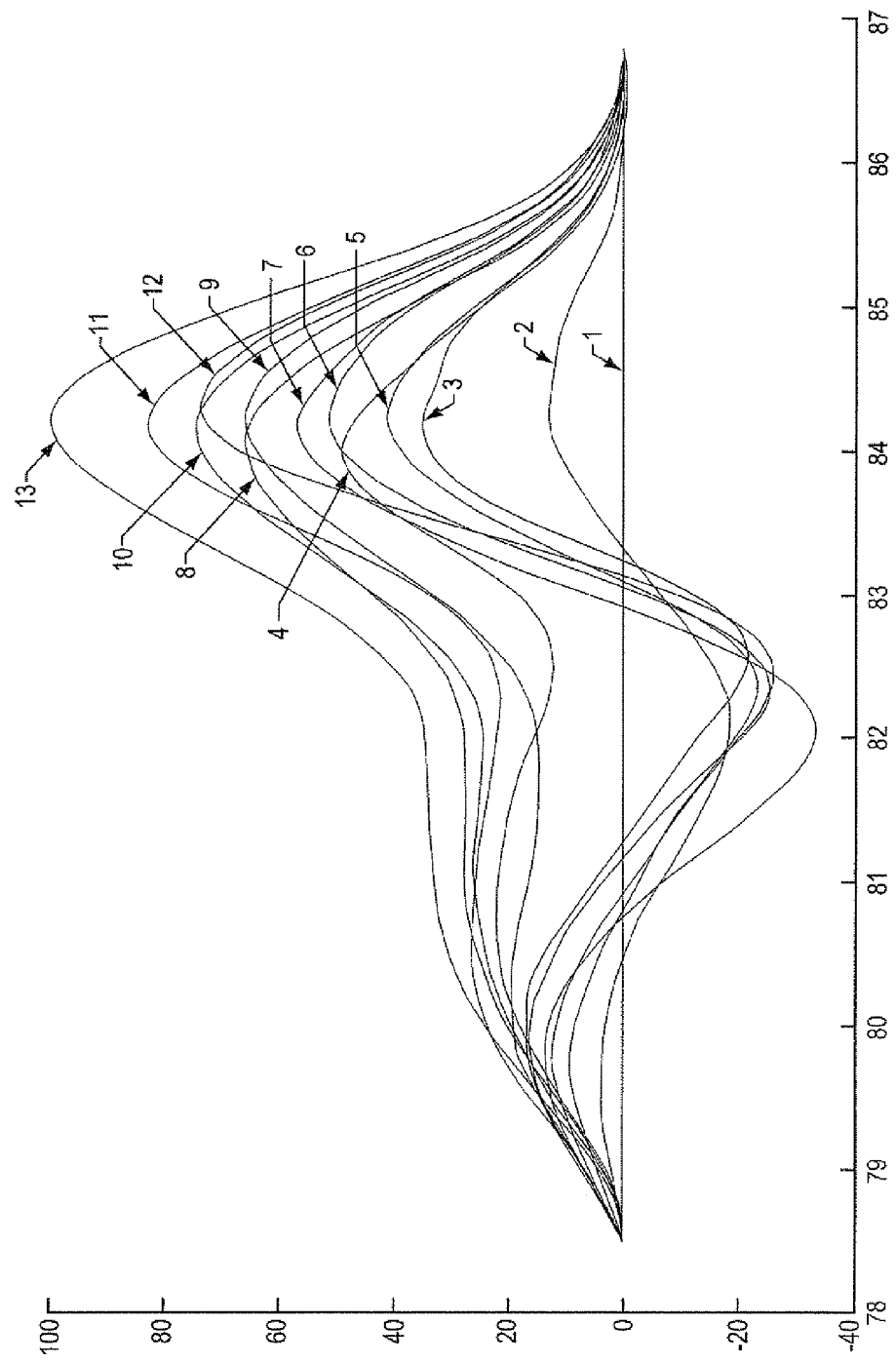
FIG. 12 is a graphical form of the experimental data of FIG. 11.

According to various embodiments of methods for the analysis of dissociation melt curve data, the experimental melt curve data can be further analyzed to detect true differences in data that are different by only fraction of a degree. According to various embodiments, in step 150 of FIG. 2, difference data may be generated using the experimental data. A plot of difference data for a set of experimental data is displayed in FIG. 12, and the corresponding samples are shown in the table of FIG. 11. In FIG. 12, the melt curve data for the wild type sample is taken as the data from which all other melt curve data for all other samples will be compared. The differences are taken between the melt curve data, and the wild type, and plotted in FIG. 12. The scale on the abscissa is set as previously described. The ordinate scale is a relative scale based on the reference melt curve data defined as zero, by definition, and the minimum and maximum values set by greatest magnitude offset in the difference data. The data of interest corresponds to the attributes of the peaks in the positive region of the scale. The difference plots in FIG. 12 are labeled with respect to the corresponding samples listed in the table of FIG. 11.

In the table of FIG. 11, the melting temperature, $T_m$, is shown in the first column for the samples. In the second column, designated Delta Max, the values entered in that column refer to the value on the relative scale of the difference between the wild type and a sample peak, for the peaks in the positive region of the scale. In the third column, $T_{Deltamax}$ is the corresponding temperature at Delta Max. In the last column, the sum of the absolute difference (SAD) is the area under the sample peak. Therefore, various embodiments of step 150 of FIG. 2 are demonstrated in FIG. 11 and FIG. 12, in which the creation of difference data, as shown in the plots of FIG. 12, becomes the basis of generating feature vectors in addition to the melting temperatures, such as Delta Max, $T_{Deltamax}$, and SAD.

Figure 2:
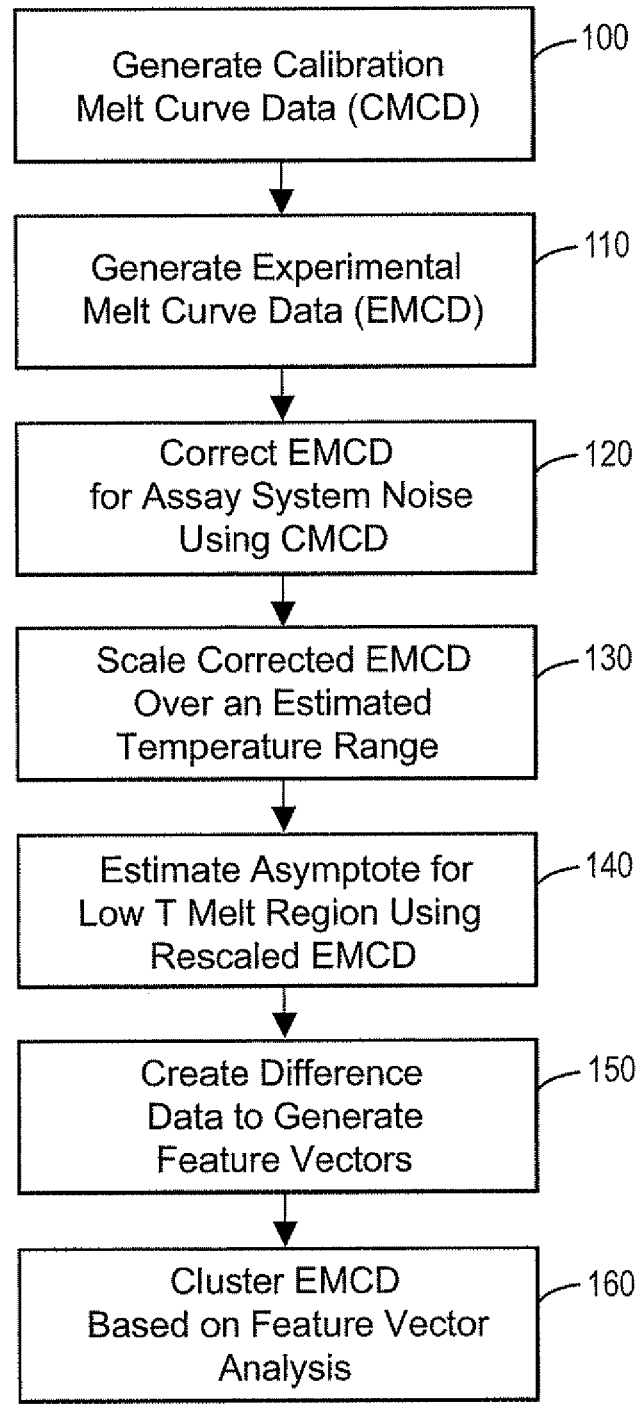
FIG. 2 is a flow chart that depicts various embodiments of methods for the analysis of dissociation melt curve data.

According to various embodiments of methods for the analysis of dissociation melt curve data as indicated by step 160 of FIG. 2, the feature vectors can be used to further discriminate differences in a set of data, where the melting temperatures are different by only a fraction of a degree. For example, in the table of FIG. 11, the samples are known to be samples that should not be clustered. That is, unlike the data represented in FIG. 9, for which there were multiple samples, or clusters of samples, for a genotype, for the data represented in FIG. 11, the samples should be distinct. Using the features vectors provides more information for which samples having melting temperatures that are different by only a fraction of a degree may be further discriminated. Through the inspection of the data in the table of FIG. 11, it is apparent that sample 2, having a $T_m$ of 84.1° C. is different from samples 3 and 4, which have the same $T_m$ of 84.2° C., by only 0.1° C. However, the Delta Max for the three samples is strikingly different, and clearly differentiates them. In this regard, the use of an additional feature vector may be used to further discriminate the samples.

Likewise, the block of data indicated with hatching; samples 5-10, all have melting temperatures of 84.5° C. Though most of the samples may be further discriminated by using Delta Max, samples 8 and 9 are only distinguished using the SAD feature vector. According to various embodiments of methods for the analysis of dissociation melt curve data in step 160 of FIG. 2, some or any combination of the feature vectors may be used to further evaluate EMCD. In various embodiments of step 160 of FIG. 2, the EMCD may be sorted by feature vectors sequentially, and an evaluation of fit may be made at after each iteration. According to various embodiments of step 160 of FIG. 2, the EMCD may be sorted by one feature vector or any combination of feature vectors as an iterative process, and an evaluation of the data may be evaluation of fit may be made after each iteration While the principles of this invention have been described in connection with specific embodiments of methods for analyzing dissociation melt curve data, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A method for analyzing melt curve data, the method comprising:
    generating, by a computer system, melt curve data for a calibration sample deposited in a plurality of support regions of a sample support device in a thermal cycler system, wherein the melt curve data is a calibration set of melt curve data, operable for correcting other sets of melt curve data;
    generating, by the computer system, melt curve data for at least one test sample deposited in a plurality of support regions of a sample support device in thermal cycler system, wherein the melt curve data is an experimental set of melt curve data;
    correcting, by signal processing by the computer system, the experimental set of melt curve data for system noise variation over the plurality of support regions of the sample support using the calibration set of melt curve data; and
    displaying, by the computer system, the corrected experimental set of melt curve data to a user.

2. The method of claim 1, wherein the correction is done on a derivative form of the melt curve data.

3. The method of claim 1, wherein the at least one test sample is a plurality of test samples.

4. The method of claim 3, further comprising the step of scaling the corrected experimental set of melt curve data over an estimated temperature range.

5. The method of claim 4, further comprising the step of fitting the scaled experimental set of melt curve data to an estimated asymptote for a low temperature region of a melting region of the melt curve data.

6. The method of claim 5, further comprising the step of clustering the experimental set of melt curve.

7. The method of claim 5, further comprising the step of creating difference data from the corrected experimental set of melt curve data, wherein the melt curve data for a test sample in the plurality of samples is selected as a reference, and the melt curve data for the remaining samples are subtracted from the reference.

8. The method of claim 7, further comprising the step of generating a set of feature vectors from the difference data, wherein a feature vector is an attribute used to cluster the experimental set of melt curve data into subgroups.

9. The method of claim 8, and further comprising the step of clustering the experimental set of melt curve data into subgroups based on at least one feature vector.

10. The method of claim 1, wherein the correction of the experimental set of melt curve data using the calibration set of melt curve data is a correction for assay system noise.

11. The method of claim 10, wherein the source of assay system noise is thermal non-uniformity.

12. The method of claim 10, wherein the source of assay system noise is excitation source non-uniformity.

13. The method of claim 10, wherein the source of assay system noise is detection noise.

14. The method of claim 1, wherein curve fitting steps are performed on the calibration set of melt curve data.

15. The method of claim 14, further comprising estimating an asymptote at a low temperature end based on the calibration set of melt curve data.

16. A method for analyzing melt curve data, the method comprising:
    generating, by a computer system, melt curve data for a calibration sample deposited in a plurality of support regions of a sample support device in a thermal cycler system, wherein the melt curve data is a calibration set of melt curve data;
    generating, by the computer system, melt curve data for at least one test sample deposited in a plurality of support regions of a sample support device in thermal cycler system, wherein the melt curve data is an experimental set of melt curve data;

correcting, by signal processing by the computer system, the experimental set of melt curve data using the calibration set of melt curve data, wherein the correction of the experimental set of melt curve data by the calibration set of melt curve data removes system variance over the plurality of support regions from the experimental set of melt curve data;

analyzing, by the computer system, the corrected experimental set of melt curve data, wherein the removal of system variance from the experimental set of melt curve data enhances analysis of small variations within the experimental set of melt curve data; and displaying the corrected experimental set of melt curve data.

17. The method of claim 16, wherein the sample support device with a calibration sample deposited in a plurality of support regions and the sample support device with at least one test sample deposited in a plurality of support regions are different sample support devices.

18. The method of claim 16, wherein the sample support device with a calibration sample deposited in a plurality of support regions and the sample support device with at least one test sample deposited in a plurality of support regions are the same support device.

19. A system for analyzing melt curve data, the system comprising:

a detection system configured to:
generate melt curve data for a calibration sample deposited in a plurality of support regions of a sample support device in a thermal cycler system, wherein the melt curve data is a calibration set of melt curve data, operable for correcting other sets of melt curve data, generate melt curve data for at least one test sample deposited in a plurality of support regions of a sample support device in thermal cycler system, wherein the melt curve data is an experimental set of melt curve data; and a computer system configured to:
correct, by signal processing, the experimental set of melt curve data for system noise variation over the plurality of support regions of the sample support using the calibration set of melt curve data, and display the corrected experimental set of melt curve data to a user.

20. The system of claim 19, wherein the correction is done on a derivative form of the melt curve data.

21. The system of claim 19, wherein the at least one test sample is a plurality of test samples.

22. The system of claim 21, wherein the computer system is further configured to scale the corrected experimental set of melt curve data over an estimated temperature range.

* * * * *